United States Patent
Baker et al.

[11] Patent Number: 5,971,940
[45] Date of Patent: Oct. 26, 1999

[54] SURGICAL INSTRUMENT WITH LOCKING FEATURE, SPLIT DISTAL HOUSING, AND SHARPENED JAWS

[75] Inventors: Eric Baker; Brian Cran, both of Seattle; Mark E. Plaia, Redmond; Vito Monni, Seattle, all of Wash.

[73] Assignee: SCIMED Life Systems, Inc., Maple Grove, Minn.

[21] Appl. No.: 09/027,483

[22] Filed: Feb. 20, 1998

[51] Int. Cl.⁶ .................................................. A61B 10/00
[52] U.S. Cl. ............................................................ 600/567
[58] Field of Search ................................. 600/562, 564, 600/567; 606/205

[56] References Cited

U.S. PATENT DOCUMENTS

| | | | |
|---|---|---|---|
| 4,815,476 | 3/1989 | Clossick | 128/751 |
| 4,887,612 | 12/1989 | Esser et al. | 128/751 |
| 5,147,380 | 9/1992 | Hernandez et al. | 606/207 |
| 5,184,625 | 2/1993 | Cottone, Jr. et al. | 128/751 |
| 5,251,638 | 10/1993 | Cottone, Jr. et al. | 128/751 |
| 5,391,180 | 2/1995 | Tovey et al. | 606/205 |
| 5,431,675 | 7/1995 | Nicholas et al. | 606/170 |
| 5,476,099 | 12/1995 | Robinson et al. | 600/564 |
| 5,490,861 | 2/1996 | Kratsch et al. | 606/205 |
| 5,496,317 | 3/1996 | Goble et al. | 606/48 |
| 5,507,773 | 4/1996 | Huitema et al. | 606/207 |
| 5,562,700 | 10/1996 | Huitema et al. | 606/207 |
| 5,611,808 | 3/1997 | Hossain et al. | 606/170 |
| 5,620,459 | 4/1997 | Lichtman | 606/205 |
| 5,626,597 | 5/1997 | Urban et al. | 606/170 |
| 5,667,526 | 9/1997 | Levin | 606/207 |

OTHER PUBLICATIONS

"BYCEP Single–Use Endomyocardial Biopsy Forceps" marketing materials, EP Technologies, 5 pages 1996.
"Disposable Cordis Biopsy Forceps" marketing materials, Cordis Corporation, 13 pages 1988.
"Endomyocardial Biopsy Forcep" marketing materials, ARGON Medical, 4 pages 1992.
"Disposable Biopsy Forceps" marketing materials, Cook Incorporated, 5 pages 1989.
"FEHLING Bioptome System" marketing materials, INRAD, 8 pages 1987.

*Primary Examiner*—Max Hindenburg
*Attorney, Agent, or Firm*—Christensen O'Connor Johnson & Kindness PLLC

[57] ABSTRACT

A biopsy forceps having a proximal end and a distal end. The biopsy forceps includes a handle at the proximal end of the biopsy forceps. The handle includes a body portion and an actuator axially displaceable relative to the body portion. The biopsy forceps further includes an end effector assembly at the distal end of the biopsy forceps. The end effector assembly includes a pair of opposed end effectors operable between an open position and a closed position. A catheter portion connects the handle to the end effector assembly so that axial displacement of the actuator relative to the body portion causes the end effectors to move between the open position and the closed position. The handle is shaped to receive the catheter portion to lock the end effectors in the open position.

30 Claims, 9 Drawing Sheets

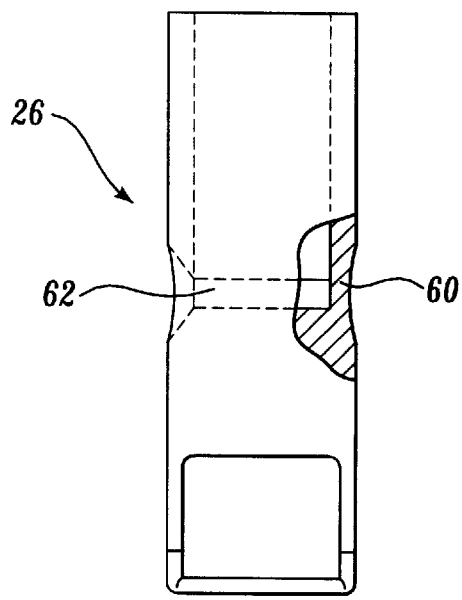
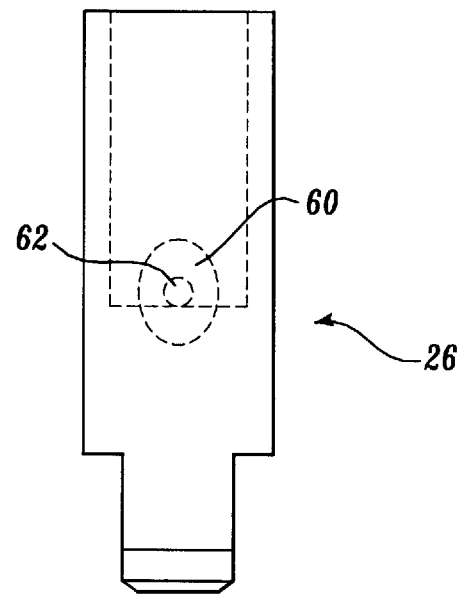
*Fig. 13A.*   *Fig. 13B.*
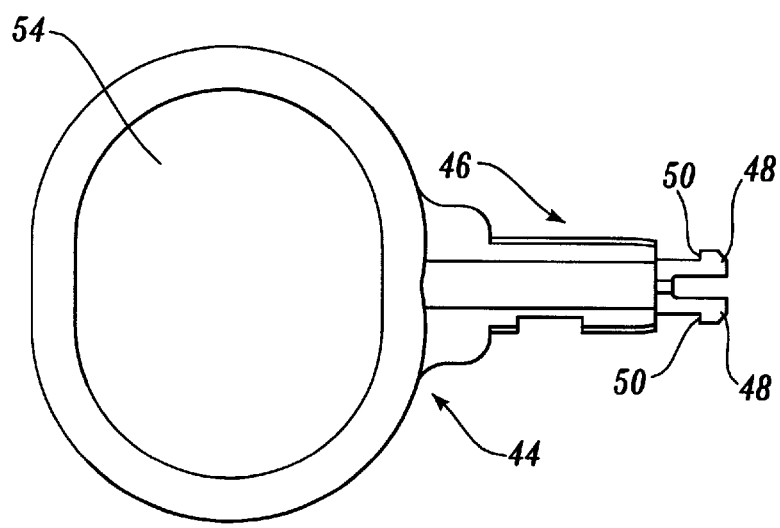
*Fig. 14.*

3. Surgical Instrument with Locking Feature, Split Distal Housing, and Sharpened Jaws

BACKGROUND OF THE INVENTION

1. Field of the Invention

The present invention relates to surgical instruments. More particularly, this invention relates to a surgical instrument, such as a biopsy forceps device, that includes a locking feature for maintaining end effectors in an open relation during removal of a tissue sample, and relates to a related method of removing a tissue sample.

2. Background of the Related Art

An endomyocardial biopsy forceps device is used to obtain biopsy tissue samples from the interior walls of heart chambers. Such samples are often used to characterize rejection factors in the hearts of transplant recipients or for other diagnostic applications.

A typical biopsy forceps includes a long flexible catheter portion having a pair of opposed jaws at a distal end and a manual actuator at the proximal end. Manipulation of the actuator opens and closes the jaws.

During a biopsy tissue sample procedure, the physician first inserts the catheter portion into an appropriately sized introducer sheath. Under ultrasound or other visual technique, the physician then guides the catheter portion through a long tortuous passageway, such as a vein or an artery, until the jaws are positioned by a tissue sample site of an interior wall of the chamber. The physician then opens the jaws, positions the jaws around the tissue to be sampled, and manipulates the actuator so that the jaws close around the tissue. A sample of the tissue is then cut from the biopsy site while it is trapped between the jaws. Keeping the jaws closed, the physician withdraws the biopsy forceps and opens the jaws to collect the biopsy tissue sample.

During removal of a tissue sample from the device, the physician must maintain the jaws in an open relationship. With conventional endomyocardial biopsy forceps, the physician must manipulate the actuator handle to maintain the open relationship and, at the same time, remove the sample. Performing both of these steps at the same time typically requires the aid of another person. The need exists therefore for a biopsy forceps and a related method in which tissue samples can be removed more easily.

Conventional endomyocardial biopsy forceps typically also include an end effector assembly made of multiple parts requiring rivets or other fasteners to hold the assembly together. Such a construction increases the manufacturing cost and assembly time. An end effector assembly with less parts and a simpler construction therefore is desired.

The end effector assembly retains the opposed jaws. Each jaw typically includes a cup at its distal end to retain the biopsy sample. The edges of the cup perform the cutting operation. Because the jaw is small and difficult to machine and the edges must be very sharp, conventional machining techniques often result in rough, pitted jaws with burrs. Therefore, a process for achieving a burr free, polished jaw with sharp edges and an acceptable cosmetic appearance is desired.

SUMMARY OF THE INVENTION

Objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, a biopsy forceps is provided having a proximal end and a distal end. The biopsy forceps includes a handle at the proximal end having a body portion and an actuator axially displaceable relative to the body portion. The biopsy forceps further includes an end effector assembly at the distal end. The end effector assembly includes a pair of opposed end effectors operable between an open position and a closed position. A catheter portion connects the handle to the end effector assembly so that axial displacement of the actuator relative to the body portion causes the end effectors to move between the open position and the closed position. The handle is shaped to receive the catheter portion to lock the end effectors in the open position.

According to another aspect of the invention, a biopsy forceps is provided having a proximal end and a distal end. The biopsy forceps includes a handle at the proximal end having a body portion and an actuator axially displaceable relative to the body portion. The biopsy forceps includes an end effector assembly at the distal end. The end effector assembly includes a pair of opposed end effectors operable between an open position and a closed position. A catheter portion connects the handle to the end effector assembly so that axial displacement of the actuator relative to the body portion causes the end effectors to move between the open position and the closed position. The biopsy forceps includes means associated with the handle for locking the end effectors in the open position to facilitate removal of a biopsy sample.

According to a further aspect of the invention, a method of obtaining a biopsy sample from a patient's body is provided. The method includes the step of providing a biopsy forceps having a handle at a proximal end of the forceps, an end effector assembly at a distal end of the forceps, and a catheter portion connecting the handle to the end effector assembly. The end effector assembly includes a pair of opposed end effectors operable between an open position and a closed position. The method further includes the steps of inserting the end effector assembly and the catheter portion into the patient's body so that the end effectors are positioned at a tissue sample site, obtaining a biopsy sample, withdrawing the catheter portion and the end effector assembly from the patient's body with the end effectors in the closed position, retaining the catheter portion in the handle so that the handle locks in a position corresponding to the open position of end effectors, and removing a biopsy sample from the end effectors.

According to a yet further aspect of the invention, a method of sharpening an edge of a jaw for use in a surgical instrument is provided. The method includes the steps of connecting the jaw to a first terminal of a power supply, placing the jaw in a chemical solution containing a second terminal of the power supply, and delivering electric current between the first terminal and the second terminal to sharpen the edge of the jaw.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate an embodiment of the invention and together with the description, serve to explain the principles of the invention. In the drawings.

FIGS. 13A and 13B are side elevation views of a finger grip insert for use in the handle assembly of FIG. 2A;

FIG. 14 is a top elevation view of a thumb ring for use in the handle assembly of FIG. 2A;

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

The present invention is directed towards a biopsy forceps device, and a related method, that includes structure for locking the end effectors, typically jaws, in an open position during removal of the tissue sample. At the same time, the proximal actuation handle remains locked in the position corresponding to the open jaw position. In this way, both of the physician's hands may be free from the actuation handle and used to obtain the tissue sample from the jaws. The biopsy forceps according to the present invention also includes a novel end effector assembly including a split housing to be described in detail herein and jaws that are sharpened and polished at the same time using an electrosharpening chemical process.

The biopsy forceps device according to the present invention is described below and shown in the figures in connection with an endomyocardial biopsy forceps, and particularly a single sample reusable forceps. The invention described herein, however, is fully capable of being incorporated into all biopsy forceps, including multiple sample biopsy forceps, endoscopic biopsy forceps for use in the gastrointestinal tract, urological biopsy forceps for use in the urinary tract, biliary biopsy forceps, and other similar biopsy forceps. In addition, the invention described herein may be used in connection with other types of surgical instruments, such as graspers, that include opposed end effectors other than jaws that move with respect to each other.

Figure 1:
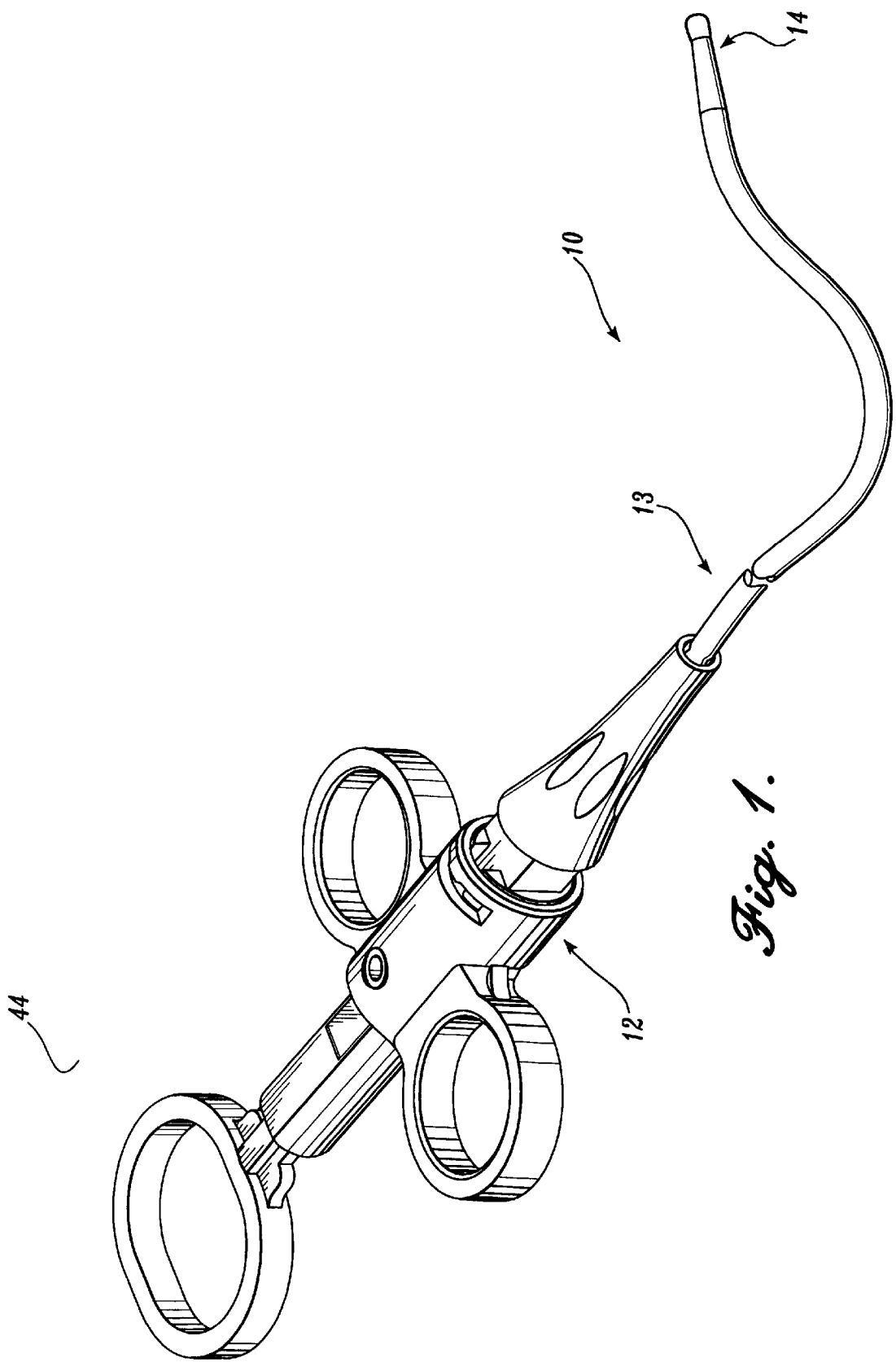
FIG. 1 is a perspective view of a preferred embodiment of a surgical instrument, and particularly an endomyocardial biopsy forceps according to the present invention.

FIG. 1 shows an endomyocardial biopsy forceps 10 according to the present invention. Biopsy forceps 10 includes three main components: a handle 12 at the proximal end of biopsy forceps 10; an end effector assembly 14 at the distal end of biopsy forceps 10; and a long, flexible catheter portion 13 that connects handle 12 to end effector assembly 14.

Figure 2:
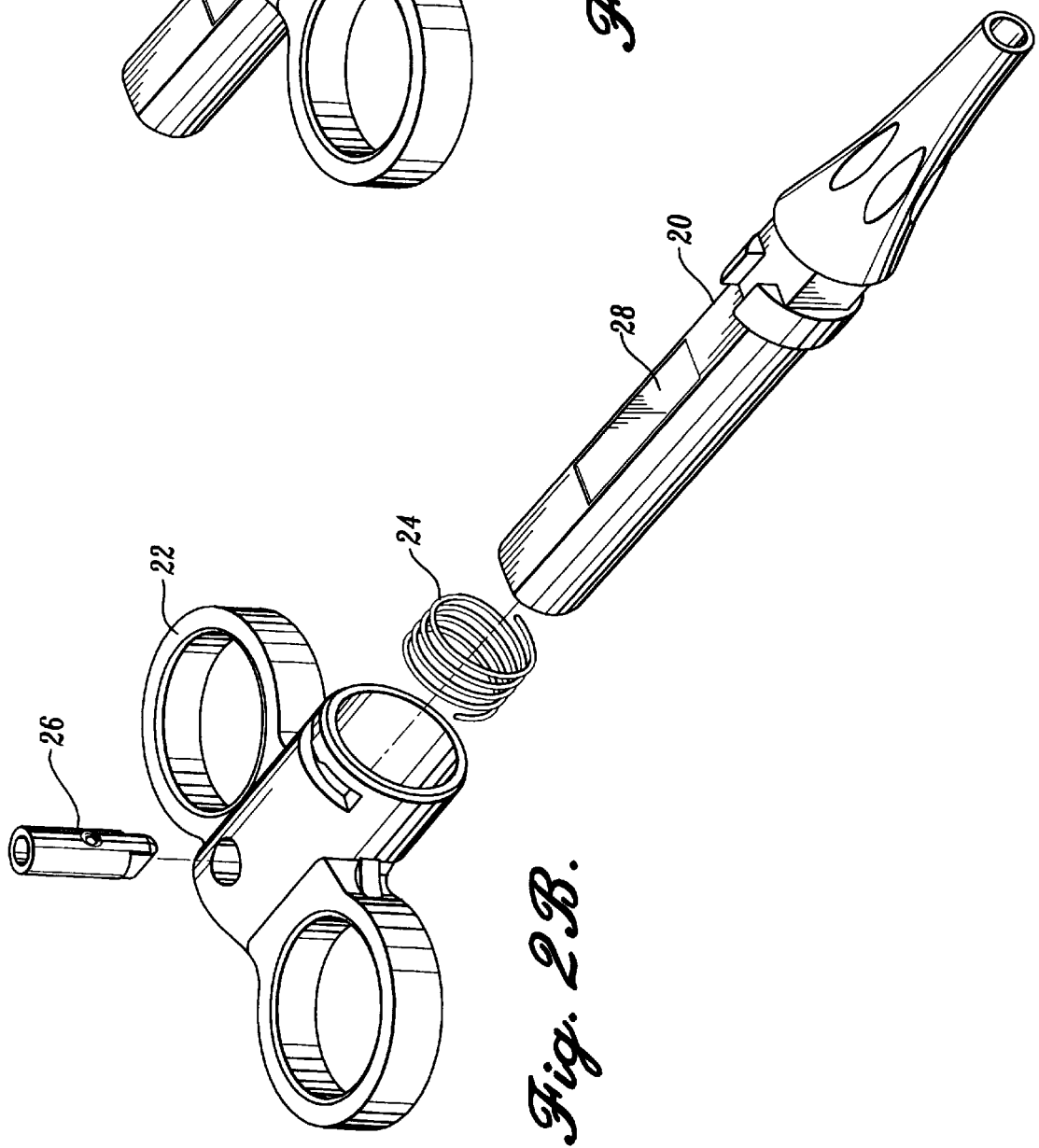
FIG. 2A is a perspective view of a portion of a handle assembly according to an embodiment of the present invention and for use in the endomyocardial biopsy forceps of FIG. 1.
FIG. 2B is an exploded perspective view of the portion of the handle assembly of FIG. 2A.
Figure 12:
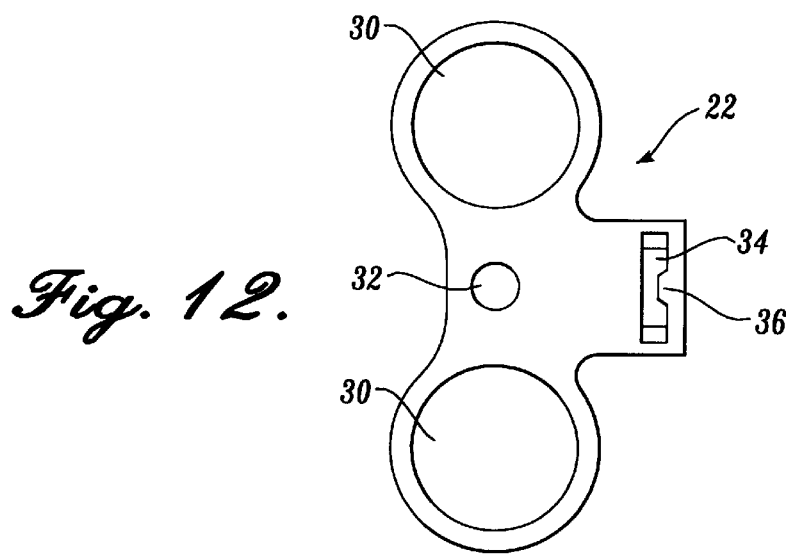
FIG. 12 is a top elevation view of a finger grip for use in the handle assembly of FIG. 2A.

As shown in FIGS. 2A and 2B, handle 12 includes a handle body 20, a finger grip 22, a spring 24, a finger grip insert 26, and a thumb ring 44 (see FIG. 1). Finger grip 22, as shown most clearly in FIG. 12, includes a pair of holes 30 through which a physician's fingers extend for manipulation of handle 12 during actuation of the end effector assembly 14. Finger grip 22 further includes a hole 32 for insertion of finger grip insert 26, and a slot 34 and a protrusion 36 for providing the locking feature to be described in more detail below. Finger grip 22 is preferably manufactured by an injection molding process using polycarbonate or other suitable material. Finger grip 22 is generally hollow, as shown in FIG. 2B, to permit passage of handle body 20.

Figure 11A:
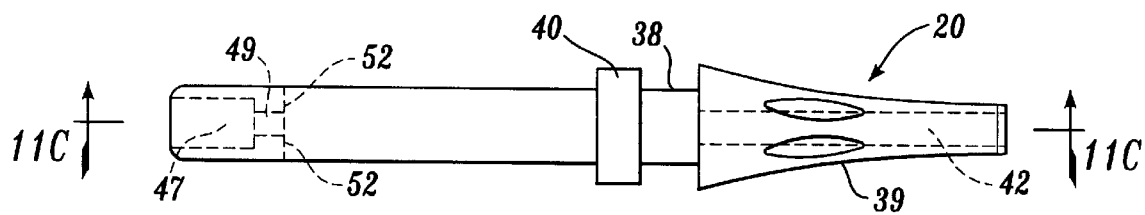
FIGS. 11A and 11B are side and top elevation views respectively of a handle body for use in the handle assembly of FIG. 2A.
Figure 11B:
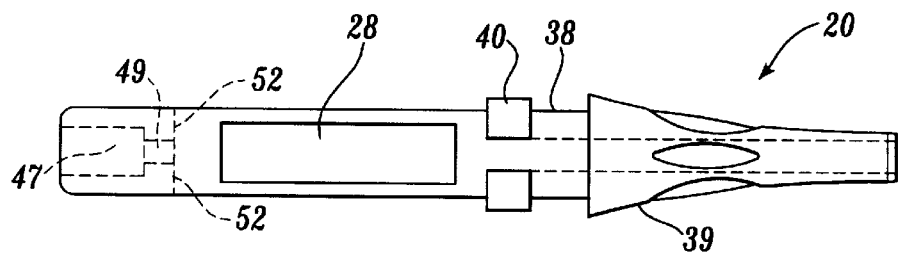
Figure 11C:
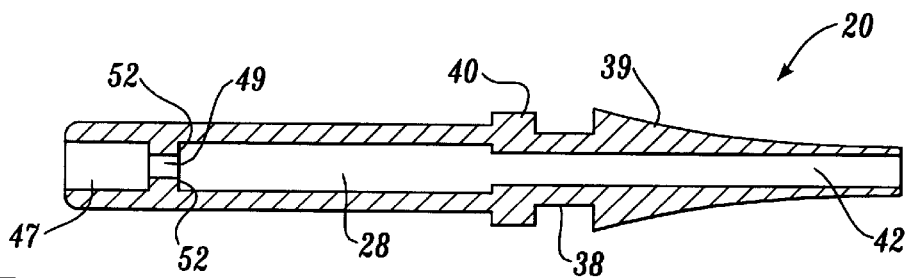
FIG. 11C is a cross-sectional view of the handle body of FIGS. 11A and 11B.

Handle body 20, as most clearly shown in FIGS. 11A to 11C, includes an open slot portion 28, and a groove 38 between a distal nose portion 39 and a stop 40. Distal nose portion 39 includes a central passageway 42. Handle body 20 is preferably injection molded from polysulfone or a similar suitable material.

Thumb ring 44, as most clearly shown in FIG. 14, includes a distal portion 46 that inserts into a proximal slot 47 of handle body 20. Distal portion 46 includes extensions 48 that flex inwardly as they pass through a central passage 49 in handle body 20 between slot 28 and slot 47. Once through passage 49, shoulders 50 of extensions 48 rest against shoulders 52 of handle body portion 20 to restrain thumb ring 44 from its removal from handle body 20. Thumb ring 44 includes a hole 54 for insertion of the physician's thumb during actuation of the end effector assembly 14. Thumb ring 44 attaches to handle body 20 so as to permit rotation of thumb ring 44 with respect to handle body 20 so that the physician's thumb may obtain a comfortable position, or orientation, during operation. Slot 47 and/or passage 49 may include ribs (not shown) to control rotation of thumb ring 44. Thumb ring 44 is preferably manufactured from an injection molded polycarbonate or other suitable material.

Finger grip insert 26, as most clearly shown in FIGS. 13A and 13B, includes a recessed area 60 leading to a passage 62 that extends through finger grip insert 26. A control wire to be described later inserts within and fixedly attaches to passage 62 in any manner known in the art. Preferably, the connection is made by an aluminum disk and stainless steel set screw not shown in the drawings. Finger grip insert 26 inserts into hole 32 of finger grip 22 and is contained within slot 28 of handle body 20. Finger grip insert 26 preferably press fits into finger grip 22 or is otherwise fixedly attached to finger grip 22.

Spring 24 rests between stop 40 of handle body 20 and the inner passageway of finger grip 22 so as to bias finger grip 22 in the proximal direction.

Figure 3:
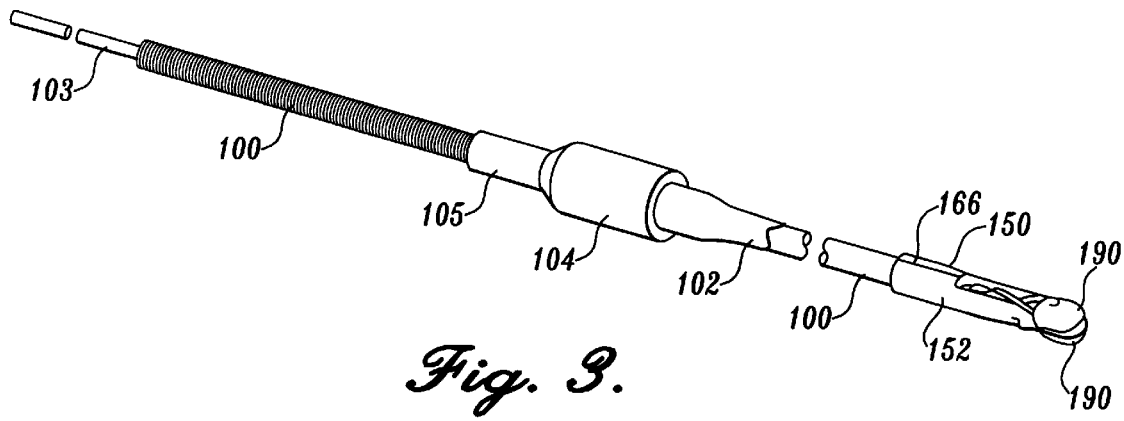
FIG. 3 is a perspective view of a flexible coil and end effector assembly according to an embodiment of the present invention and for use in the endomyocardial biopsy forceps of FIG. 1.
Figure 10:
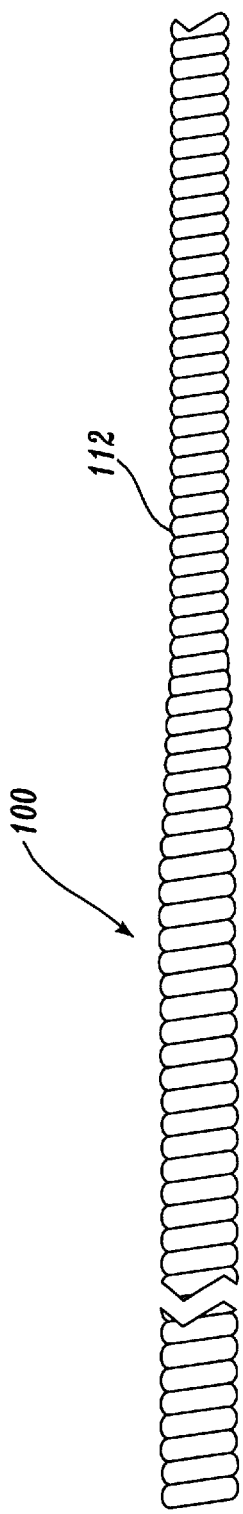
FIG. 10 is a side elevation view of a flexible coil according to an embodiment of the present invention and for use in the endomyocardial biopsy forceps of FIG. 1.

Flexible catheter portion 13 includes a flexible coil 100, as shown in FIGS. 3 and 10. An outer sheath 102 covers flexible coil 100. Flexible coil 100 is preferably made of 304 SST steel, and outer sheath 102 is preferably an extruded heat shrunk FEP material or other lubricious material. A control wire 103 extends through coil 100 and is axially movable with respect to coil 100 to operate end effector assembly 14, as will be described. Control wire 103 is preferably manufactured from a diamond drawn solid 304 SST steel. A liner 110 is provided between control wire 103 and coil 100 to lessen the friction force therebetween during respective axial movement. Liner 110 is preferably made of a TFE material or other lubricious material.

Figure 9:
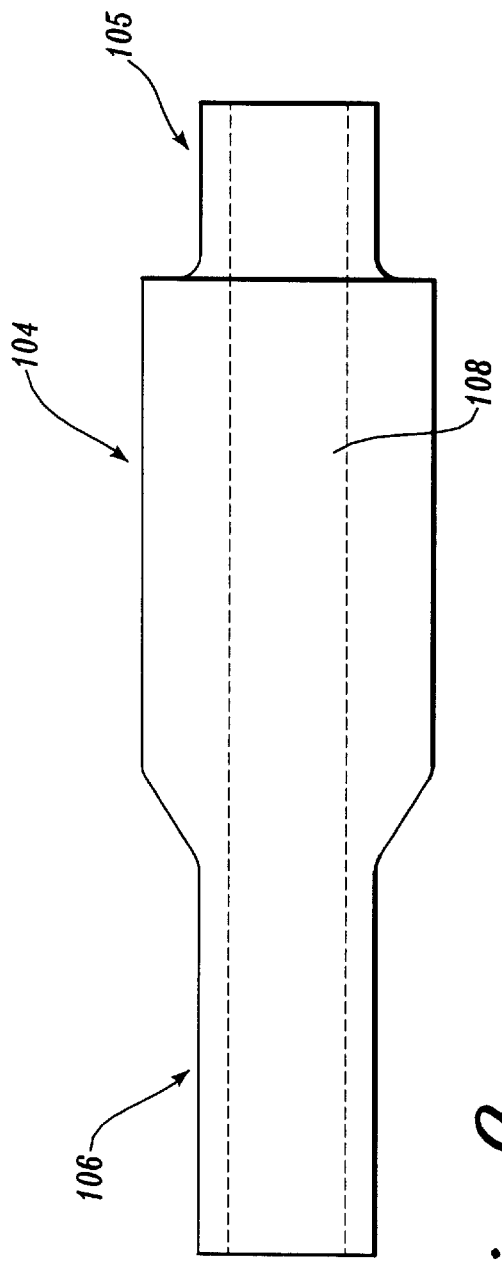
FIG. 9 is a side elevation view of a handle transition according to an embodiment of the present invention and for use in the endomyocardial biopsy forceps of FIG. 1.

Catheter portion 13 connects to handle 12 by a handle transition 104 shown in FIGS. 3 and 9. Handle transition 104 includes a distal end 105, a proximal end 106, and a centrally located passage 108. Catheter portion 13 extends through passage 108. Handle transition 104 is crimped or otherwise fixedly attached to catheter portion 13. Crimped handle transition 104 press fits into distal end portion 39 of handle body 20. Pull wire 103 extends through passage 42 and slot 28 of handle body 20 and connects to finger grip insert 26.

Figure 4:
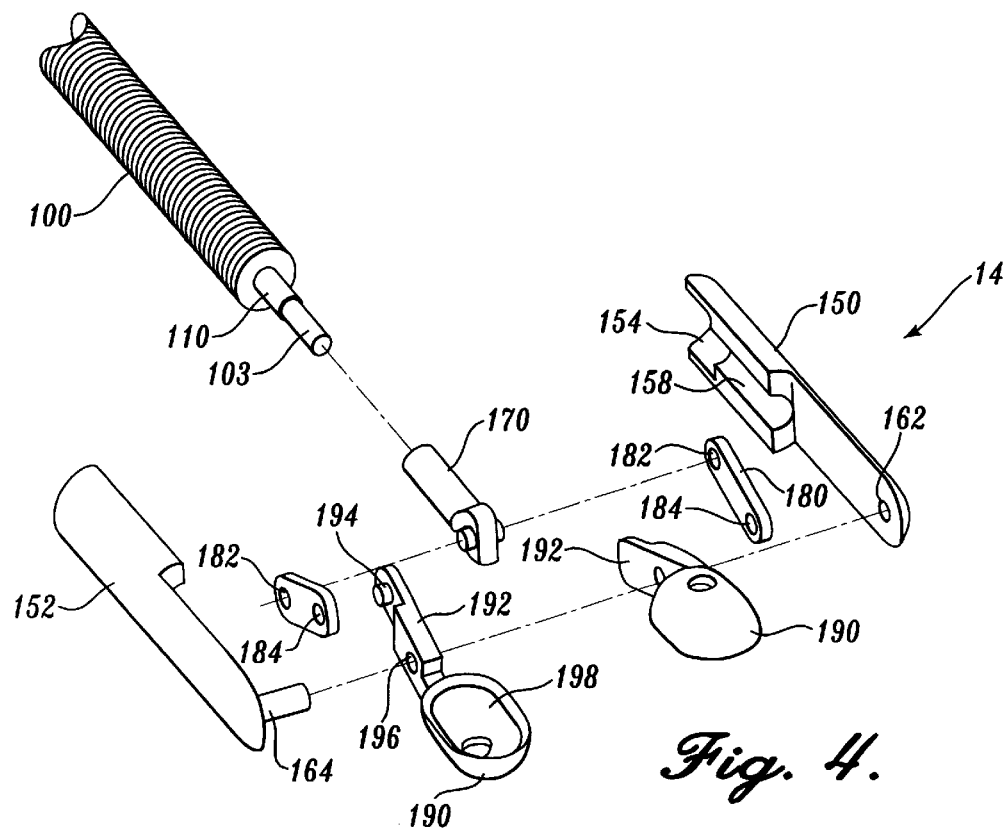
FIG. 4 is an exploded perspective view of the end effector assembly of FIG. 3.
Figure 5A:
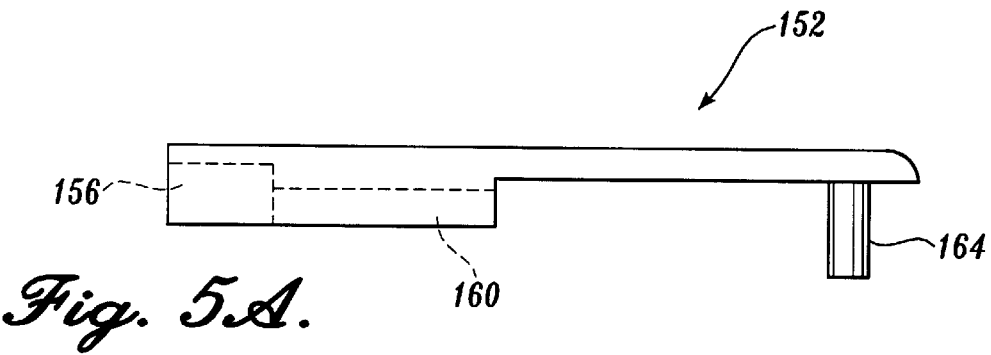
FIGS. 5A and 5B are top and side elevation views respectively of a male portion of a housing for use in the end effector assembly of FIGS. 3 and 4.
Figure 5B:
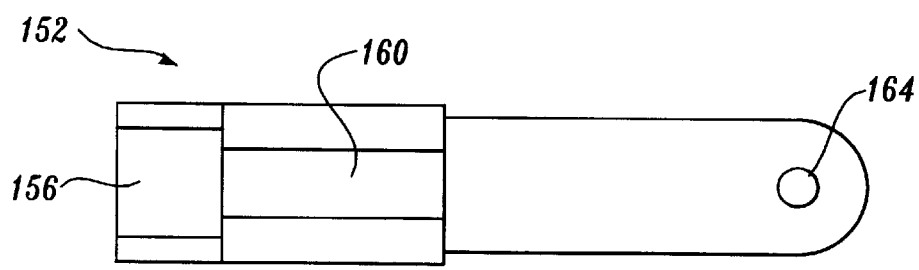
Figure 6A:
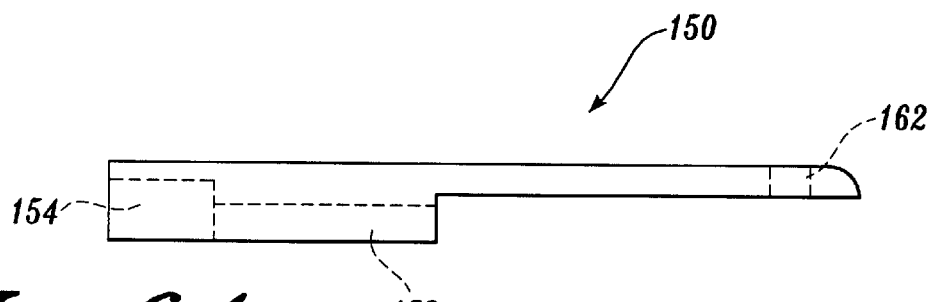
FIGS. 6A and 6B are top and side elevation views respectively of a female portion of a housing for use in the end effector assembly of FIGS. 3 and 4.
Figure 6B:
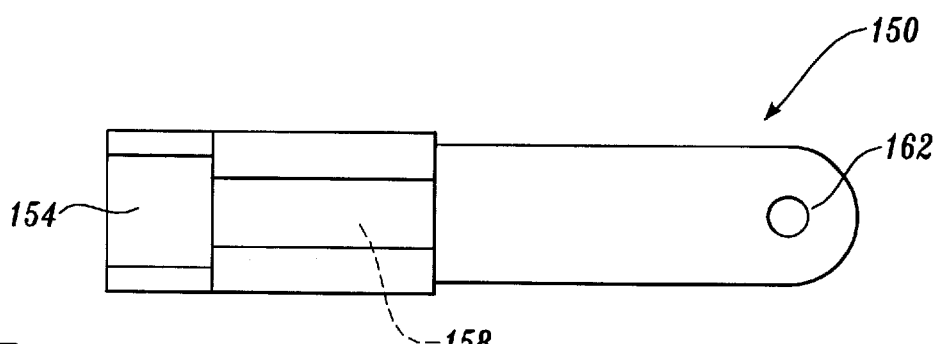

As shown in FIG. 4, end effector assembly 14 includes a two-piece housing having a female housing portion 150 that connects to a male housing portion 152. A distal actuation member 170, links 180, and jaws 190 are housed within female and male housings 150 and 152. As shown in FIGS. 5A and 5B, male housing 152 includes annular grooves 156 and 160 and a pin 164. As shown in FIGS. 6A and 6B, female housing 150 includes annular grooves 154 and 158 corresponding to grooves 156 and 160, and a hole 162 that accepts pin 164.

Female and male housings 150 and 152 are preferably manufactured from 17-4 PH stainless steel. Housings 150 and 152 sandwich together and are laser welded at interface 166 shown in FIG. 3. In addition, pin 164 is welded to hole 162. This differs from many conventional housings in that no fasteners such as rivets are used to hold the end effector assembly together. The construction according to the present invention provides for an end effector assembly that is lower cost and easier to manufacture and assemble. Links 180 are preferably manufactured from fully hardened 302 SST steel or other suitably hard material. Fully hardened steel prevents failure of the linkage assembly.

Figure 7A:
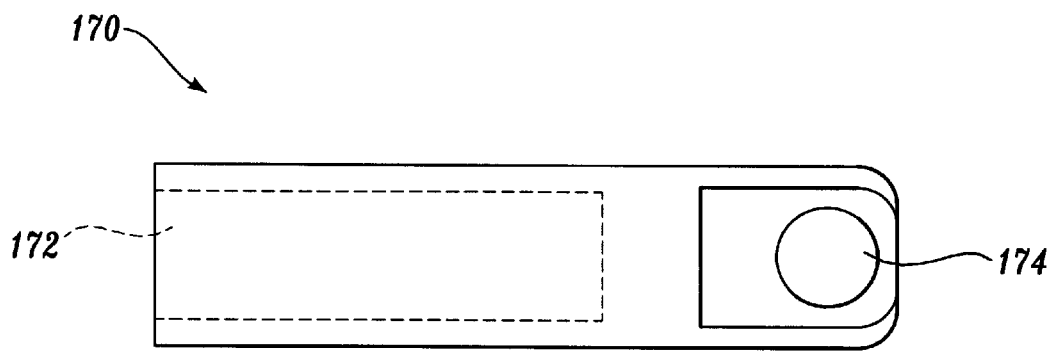
FIGS. 7A and 7B are side and top elevation views respectively of a distal actuator for use in the end effector assembly of FIGS. 3 and 4.
Figure 7B:
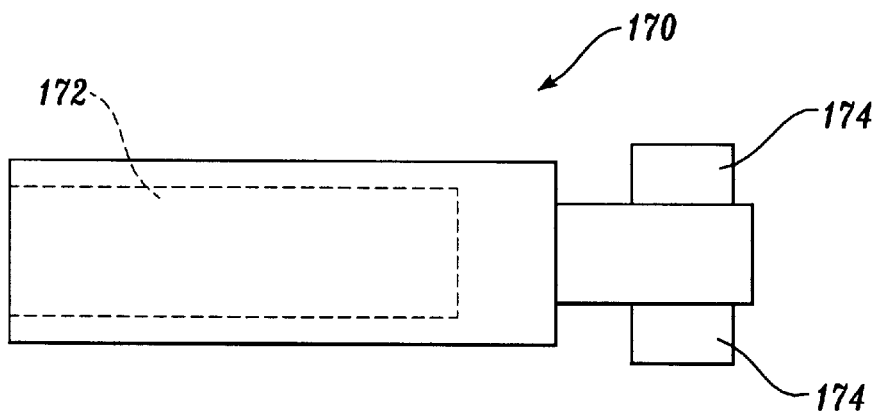

Flexible coil 100 extends into annular grooves 154 and 156 once housings 150 and 152 have been fixedly attached. Coli 100 preferably has a constant outer diameter, but may include a tapered distal section 112 (FIG. 10) that extends into grooves 154 and 156. Coil 100 is preferably laser welded to housings 150 and 152 at grooves 154 and 156. Laser welding provides superior strength to conventional methods of soldering or brazing. Control wire 103 extends from the end of coil 100 and into a passage 172 within member 170. Control wire 103 is preferably laser welded to member 170 at passage 172. As shown in FIGS. 7A and 7B, member 170 further includes pins 174 that extend through holes 182 of links 180 to connect member 170 to links 180.

Figure 8:
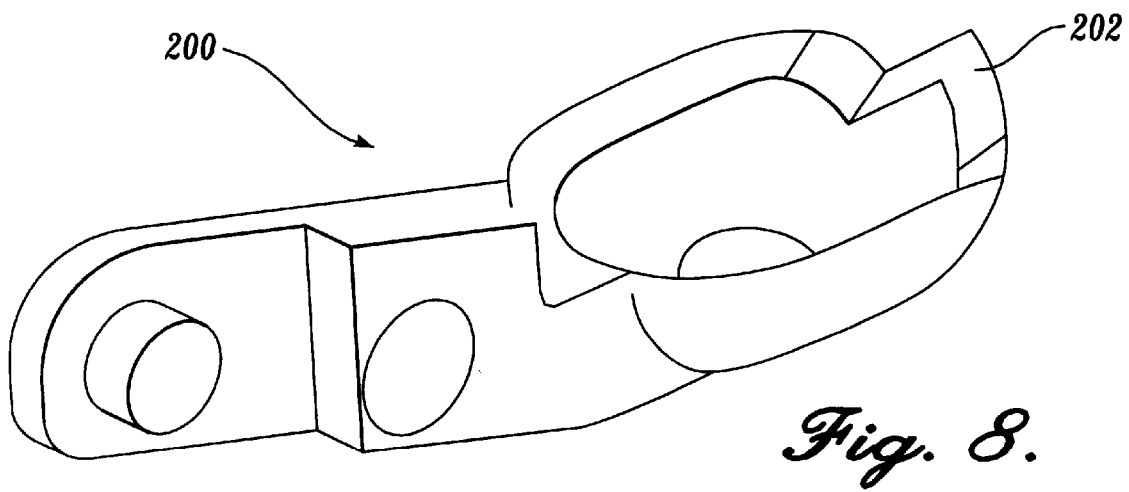
FIG. 8 is a perspective view of a jaw according to an embodiment of the present invention.

Each jaw 190 includes an arm 192 having a pin 194 and a hole 196. Each jaw 190 further includes a cup 198 for holding a biopsy tissue sample. Jaws 190 do not include teeth. It is to be understood that jaws of other configurations can be used in accordance with the present invention. For example, saber tooth jaw 200 in FIG. 8 includes teeth 202. With reference to FIG. 4, pins 194 of jaws 190 connect to links 180 at holes 184. Pin 164 of male housing 152 extends through holes 196 into recess 162 of female housing 150.

Figure 15:
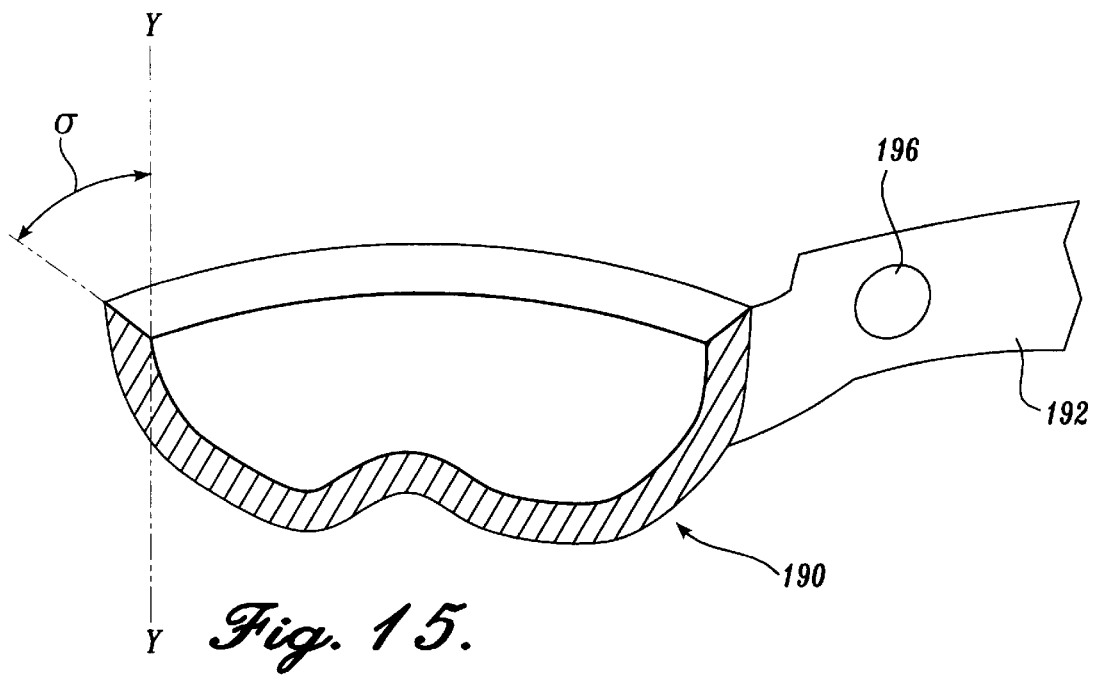
FIG. 15 is a cross-sectional view of a jaw according to the present invention.

Preferably, jaws 190 are machined or metal injection molded from 17-4 PH stainless steel. It is important that the cutting edges of jaws 190 are extremely sharp and burr free so as to cleanly cut tissue samples from the heart with a minimal amount of tearing. According to a preferred manufacturing process, the cutting edges of jaws 190 are sharpened and simultaneously polished using an electrosharpening chemical process. This process has been used conventionally to improve surface finish only (electropolishing). It has been found, however, that this process simultaneously improves surface condition and sharpens edges oriented at a specific angle. FIG. 15 shows a cross-section of a jaw 190 having an edge 191 machined at a 45 degree angle with respect to a vertical axis y—y. It has been found that use of the electrosharpening chemical process on machined angles of approximately 45 degrees results in a very sharp, burr free edge with high cutting performance. Other angles with respect to the vertical axis y—y that result in acceptably sharp, burr free edges include 30 and 60 degree angles. It is to be understood, however, that this invention may be suitable for the sharpening and polishing of edges of all angles.

Generally, the electrosharpening chemical process includes first cleaning and rinsing the part (jaw) to be sharpened and polished. The jaw is then processed in a chemical solution placed on a hot plate. Direct current removes material from the jaw and performs the electrosharpening as a stirrer agitates the solution. The jaw is then rinsed and dried.

More particularly, the electrosharpening chemical process first includes ultrasonic cleaning and degreasing a machined jaw. During ultrasonic cleaning, the jaws is placed in a beaker of cleaning solution. The cleaning solution preferably includes a mixture of 80% deionized water by volume and 20% by volume of a commercial detergent called "Alternative Cleaner 2000" available from Poly Chem Corporation. The cleaning solution is heated and used at 120 degrees F. The beaker is placed in an ultrasonic equipment tank filled with deionized water. The jaw remains immersed in the mixture for about three to five minutes as ultrasonic energy is used to clean the jaw. Other immersion times, solution temperatures, and solution concentrations may be used depending on the amount of contamination to be removed. In addition, other suitable detergents may be used for the ultrasonic cleaning.

The jaw is then rinsed using a mixture of 50% deionized water by volume and 50% isopropyl alcohol by volume. It is to be understood that other suitable rinsing solutions may be used to rinse the jaws. To prevent damage to the jaws during rinsing, the jaws are preferably rinsed in a plastic cup having a stainless steel screen at the top and numerous small holes at the bottom to permit circulation of the solution. Multiple jaws may be rinsed at one time as long as handling of the jaws is kept to a minimum to ensure that the jaws remain clean. After cleaning and rinsing of the jaw, the jaw is placed in a petri dish lined with a round lint free paper in preparation for the electrosharpening chemical process.

Figure 16:
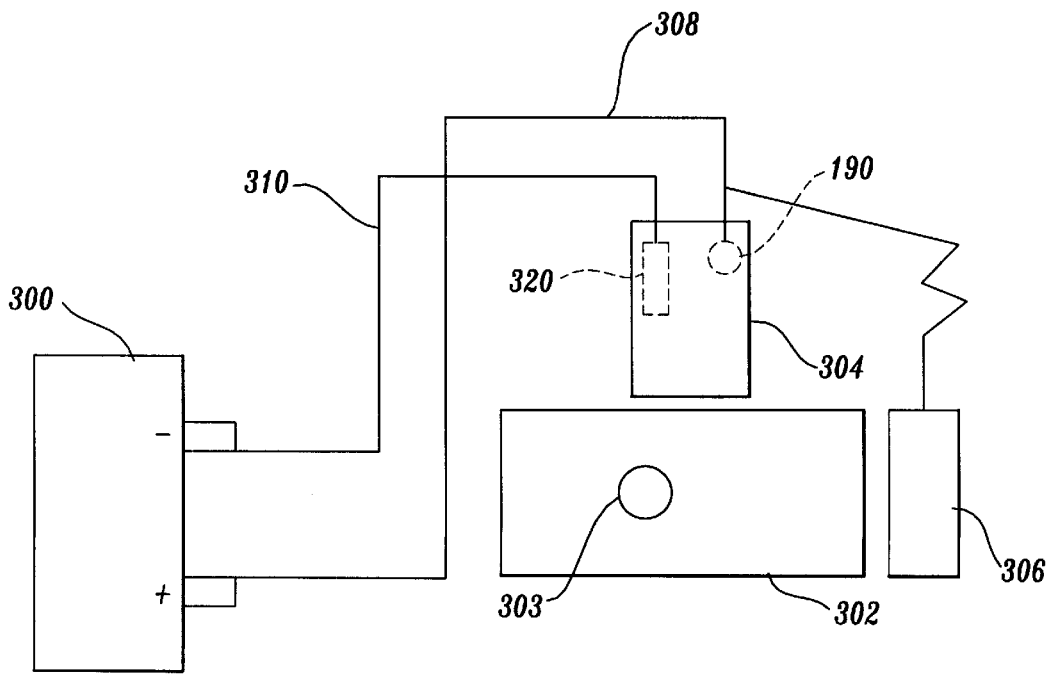
FIG. 16 is a diagram of the electrosharpening process according to the present invention.

FIG. 16 shows the general set up used in the electrosharpening chemical process. The process uses a DC variable Volts/Amps power supply 300 having a digital timer, a hot plate 302 having a stirrer 303, and a beaker 304, preferably a Pyrex 1000 ml beaker. A chemical solution substantially fills beaker 304. The solution is preferably a commercial solution of primarily phosphoric acid and glycerine called "Power Clean 500" available from Moletric Corporation. Although the solution has a virtually infinite life, periodic change, for example every 24 hours, is recommended for best results. A screen mesh type 304, 303, 316 stainless steel anode 320 connects to the negative terminal of the power supply, hangs inside beaker 304, and may be bent to conform to the shape of beaker 304. A sufficiently thick cable 310, at least 16 gage, connects anode 320 to the negative terminal. The positive terminal of power supply 300 connects to a heavy gold plated clip by a cable 308. The clip (not shown) represents the cathode and hangs in the solution during the electrosharpening chemical process. A preferable anode/cathode ratio for the process is 100/1, and a preferable current density is 60/100 amps/ft square. The process preferably occurs at room temperature.

To begin the electrosharpening chemical process, the jaw is connected to the gold plated clip so that the cutting edge of the jaw faces anode 320 and is spaced about one inch from the anode. The jaw is lowered sufficiently into the solution within beaker 304 so that the jaw, and not the gold clip, is sharpened and polished. A laboratory jack 306 with a stand may be used to lower the jaw into the solution. Stirrer 303 of hot plate 302 is set to a suitable level of agitation so that the chemicals do not settle and to promote flow between the cathode and the anode. Power supply 300 is set to a suitable voltage, preferably 12 volts, and its timer is set to a sufficient amount of time, preferably about 11 seconds. A start button of power supply 300 is pushed to activate the current and the timer, and the electrosharpening of the jaw takes place. After the set time expires, the jaw is lifted from the solution.

Then, the jaw is rinsed using a mixture of 50% deionized water by volume and 50% isopropyl alcohol by volume, or another suitable rinsing solution, with a separate hot plate and mixer. Thereafter, the jaw is air dried preferably under a fume hood.

In the electrosharpening chemical process just described, different size jaws may require adjustments to, for example, the time in the phosphoric acid base solution, the temperature of the hot plate, the type of anode or cathode material, the composition or concentration of the phosphoric acid base solution or rinse solution, the type or amount of agitation, the distance between the anode and the cathode, and other parameters described above. It is also to be understood that the electrosharpening chemical process is applicable for other small parts, especially stainless steel parts with complex geometries, and for parts of other materials, sizes, and complex geometries requiring a sharpness not attainable by conventional methods.

The operation of the endomyocardial biopsy forceps according to the present invention will now be described. In operation, catheter portion 13 is guided through a vein or an artery of a patient until end effector assembly 14 is positioned by a tissue sample site of an interior wall of a heart chamber. The physician then opens jaws 190 by pushing finger grip 22 in the distal direction. This moves control wire 103 distally relative to coil 100 and pushes member 170 in the distal direction. Through the connection of member 170 to jaws 190 by links 180, the distal movement of actuator 170 forces jaws 190 to open around the tissue to be sampled. A sample of the tissue is then cut from the biopsy site by pulling finger grip 22 in the proximal direction to close jaws 190. The physician then withdraws catheter portion 13 from the patient. During withdrawal, the spring-loaded design keeps jaws 190 closed, ensuring retention of the sample.

To retrieve the tissue sample, the physician once again opens the jaws by pushing finger grip 22 in the distal direction. At this point, slot 34 of finger grip 22 aligns with groove 38 in handle body 20. Catheter portion 13 may then insert into slot 34 and groove 38. The physician may then permit finger grip 22 to be biased in the proximal direction by spring 24 until catheter portion 13 is retained within groove 38, against stop 40, and under protrusion 36. The compressive force supplied by spring 24 retains catheter portion 13 within groove 38. Protrusion 36 overlies catheter portion 13 to help restrain the release of catheter portion 13 from groove 38. At this point, finger grip 22 is locked in a position so that jaws 190 lock in an open position to retrieve a tissue sample. This permits the physician to remove the tissue sample from jaws 190 without the aid of another person, making sample removal easier and quicker.

It will be apparent to those skilled in the art that various modifications and variations can be made in the biopsy forceps of the present invention and in construction of this biopsy forceps without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A biopsy forceps having a proximal end and a distal end, the biopsy forceps comprising:

a handle at the proximal end of the biopsy forceps, the handle including a body portion and an actuator axially displaceable relative to the body portion;

an end effector assembly at the distal end of the biopsy forceps, the end effector assembly including a pair of opposed end effectors operable between an open position and a closed position; and a catheter portion connecting the handle to the end effector assembly so that axial displacement of the actuator relative to the body portion causes the end effectors to move between the open position and the closed position, wherein the handle is shaped to receive the catheter portion to lock the end effectors in the open position.

2. The biopsy forceps of claim 1, wherein the handle defines an opening for receiving the catheter portion to lock the end effectors in the open position.

3. The biopsy forceps of claim 2, wherein the actuator and body portion are axially locked relative to one another when the opening receives the catheter portion.

4. The biopsy forceps of claim 2, wherein the opening includes a slot in the actuator.

5. The biopsy forceps of claim 4, wherein the opening includes a groove defined by the body portion, the groove aligning with the slot when the end effectors are in the open position.

6. The biopsy forceps of claim 2, wherein the handle includes a protrusion adjacent the opening.

7. The biopsy forceps of claim 6, wherein the protrusion overlies the catheter portion when the opening receives the catheter portion.

8. The biopsy forceps of claim 2, wherein the handle includes a spring for biasing the actuator in a position corresponding to the closed position of the end effectors.

9. The biopsy forceps of claim 8, wherein the spring provides a compressive force to retain the catheter portion in the opening when the opening receives the catheter portion.

10. The biopsy forceps of claim 1, wherein the catheter portion includes an inner member and an outer member axially movable with respect to the inner member, the inner member being connected to the actuator and the end effectors.

11. The biopsy forceps of claim 1, wherein the end effectors include a pair of opposed jaws.

12. The biopsy forceps of claim 11, wherein each jaw includes a cup having a sharp edge.

13. The biopsy forceps of claim 12, wherein the sharp edge is sharpened by an electrosharpening chemical process.

14. The biopsy forceps of claim 1, wherein the end effector assembly includes a housing having a first portion coupled to a second portion for containing the end effectors.

15. The biopsy forceps of claim 14, wherein the first portion is laser welded to the second portion.

16. The biopsy forceps of claim 14, wherein the first portion includes a pin for receiving holes of the end effectors.

17. The biopsy forceps of claim 14, wherein the end effector assembly includes a distal actuation member connected to a distal end of the catheter portion and operably connected to the end effectors.

18. The biopsy forceps of claim 17, wherein the end effector assembly includes a pair of links connecting the distal actuation member to the end effectors, and wherein the first portion and the second portion contain the links.

19. A biopsy forceps having a proximal end and a distal end, the biopsy forceps comprising:

a handle at the proximal end of the biopsy forceps, the handle including a body portion and an actuator axially displaceable relative to the body portion;

an end effector assembly at the distal end of the biopsy forceps, the end effector assembly including a pair of opposed end effectors operable between an open position and a closed position;

a catheter portion connecting the handle to the end effector assembly so that axial displacement of the actuator relative to the body portion causes the end effectors to move between the open position and the closed position; and means associated with the handle for locking the end effectors in the open position to facilitate removal of a biopsy sample, wherein the locking means comprises an opening defined by the handle for receiving the catheter portion.

20. The biopsy forceps of claim 19, wherein the catheter portion is flexible so as to be capable of a position to be received by the opening.

21. The biopsy forceps of claim 19, wherein the actuator and body portion are axially locked relative to one another when the opening receives the catheter portion.

22. The biopsy forceps of claim 19, wherein the opening includes a slot in the actuator.

23. The biopsy forceps of claim 22, wherein the opening includes a groove defined by the body portion, the groove aligning with the slot when the end effectors are in the open position.

24. A method of obtaining a biopsy sample from a patient's body, the method comprising the steps of:

providing a biopsy forceps having a handle at a proximal end of the forceps, an end effector assembly at a distal end of the forceps, and a catheter portion connecting the handle to the end effector assembly, the end effector assembly including a pair of opposed end effectors operable between an open position and a closed position;

inserting the end effector assembly and the catheter portion into the patient's body so that the end effectors are positioned at a tissue sample site;

obtaining a biopsy sample;

withdrawing the catheter portion and the end effector assembly from the patient's body with the end effectors in the closed position;

retaining the catheter portion in the handle so that the handle locks in a position corresponding to the open position of end effectors; and removing a biopsy sample from the end effectors.

25. The method of claim 24, further comprising the step of flexing the catheter portion so that the handle receives the catheter portion, the flexing step occurring between the withdrawing and retaining steps.

26. The method of claim 24, wherein the end effectors include a pair of opposed jaws.

27. The method of claim 24, wherein the retaining step includes retaining the catheter portion in an opening defined by the handle.

28. The method of claim 27, wherein the retaining step includes locking an actuator of the handle in an axial position relative to a body portion of the handle.

29. The method of claim 28, wherein the opening includes a slot in the actuator.

30. The method of claim 29, wherein the opening includes a groove defined by the body portion, the groove aligning with the slot when the end effectors are in the open position.

* * * * *

UNITED STATES PATENT AND TRADEMARK OFFICE
CERTIFICATE OF CORRECTION

PATENT NO. : 5,971,940  
APPLICATION NO. : 09/027483  
DATED : October 26, 1999  
INVENTOR(S) : E. Baker et al.

It is certified that error appears in the above-identified patent and that said Letters Patent is hereby corrected as shown below:

Title Page  
Item [75] Inventors: delete "Vito Monni, Seattle,"

Signed and Sealed this

Seventeenth Day of July, 2007

JON W. DUDAS  
*Director of the United States Patent and Trademark Office*